(12) United States Patent
Messer

(10) Patent No.: US 10,085,874 B2
(45) Date of Patent: Oct. 2, 2018

(54) APPARATUS FOR SUPPORTING AN ARM DURING A MEDICAL PROCEDURE

(71) Applicant: SYNAPTIK DESIGN GROUP, LLC, Gastonia, NC (US)

(72) Inventor: Benjamin Messer, Gastonia, NC (US)

(73) Assignee: SYNAPTIK DESIGN GROUP, LLC, Gastonia, NC (US)

( * ) Notice: Subject to any disclaimer, the term of this patent is extended or adjusted under 35 U.S.C. 154(b) by 945 days.

(21) Appl. No.: 14/530,901

(22) Filed: Nov. 3, 2014

(65) Prior Publication Data

US 2016/0095738 A1  Apr. 7, 2016

Related U.S. Application Data

(63) Continuation of application No. PCT/US2014/058965, filed on Oct. 4, 2014.

(51) Int. Cl.
*A61F 5/37* (2006.01)
*A61B 6/04* (2006.01)

(52) U.S. Cl.
CPC . *A61F 5/37* (2013.01); *A61B 6/04* (2013.01)

(58) Field of Classification Search
CPC ........... A61F 5/37; A61F 5/05866; A61B 6/04
See application file for complete search history.

(56) References Cited

U.S. PATENT DOCUMENTS

2002/0128577 A1    9/2002  Smart

FOREIGN PATENT DOCUMENTS

| CA | 2343373 A1 * | 3/2000 | ......... A61F 5/05866 |
| RU | 130830 | 8/2013 | |
| SU | 1711872 | 2/1992 | |

OTHER PUBLICATIONS

Nosova, E., International Search Report for PCT/US2014/058965, dated Nov. 25, 2014, ISA/RU, Moscow, Russia.

* cited by examiner

*Primary Examiner* — Tarla Patel
(74) *Attorney, Agent, or Firm* — Trego, Hines & Ladenheim, PLLC; Brandon Trego; Jonathan Hines

(57) ABSTRACT

An apparatus for supporting an arm during medical procedures such as radial catheterization and carpal tunnel procedures is disclosed. The apparatus includes an arm support section configured to support an arm of a patient, an intermediary valley section connected to a second end of the arm support section, a wrist flexing section connected to a second end of the intermediary valley section and configured to promote a downward flexing of the wrist, and a hand-hold section connected to the wrist flexing section. The hand-hold section is configured to hold the wrist in the downward flexing position.

13 Claims, 26 Drawing Sheets

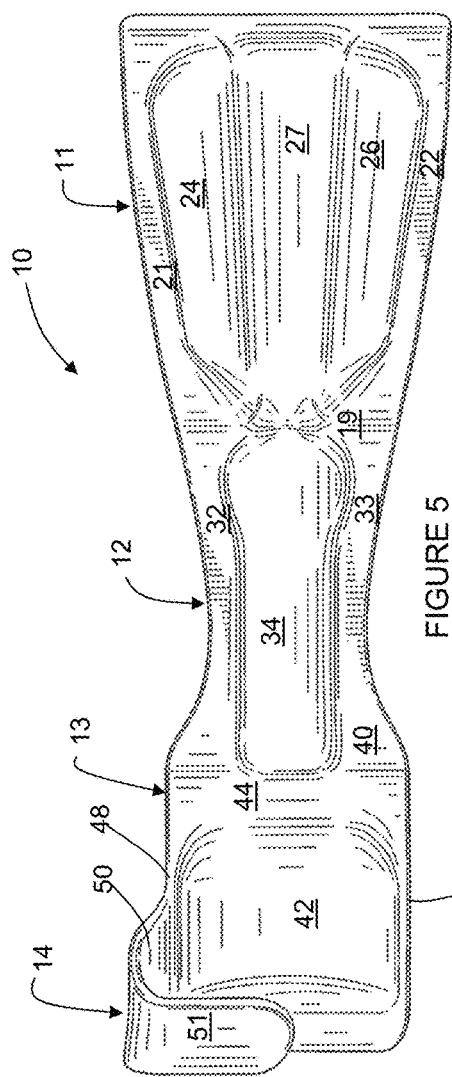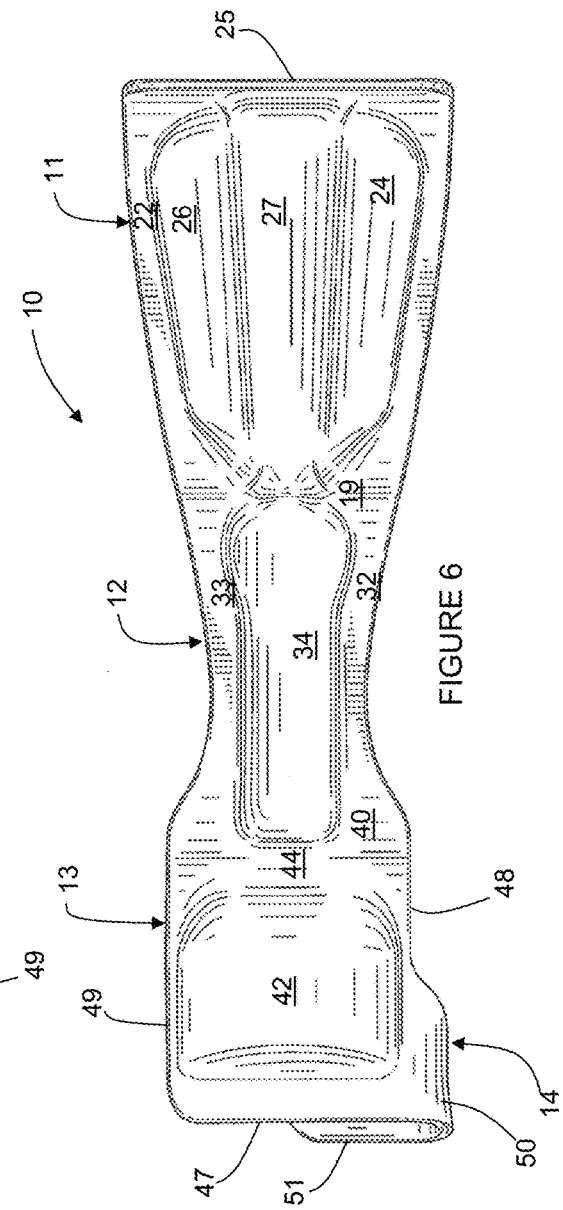

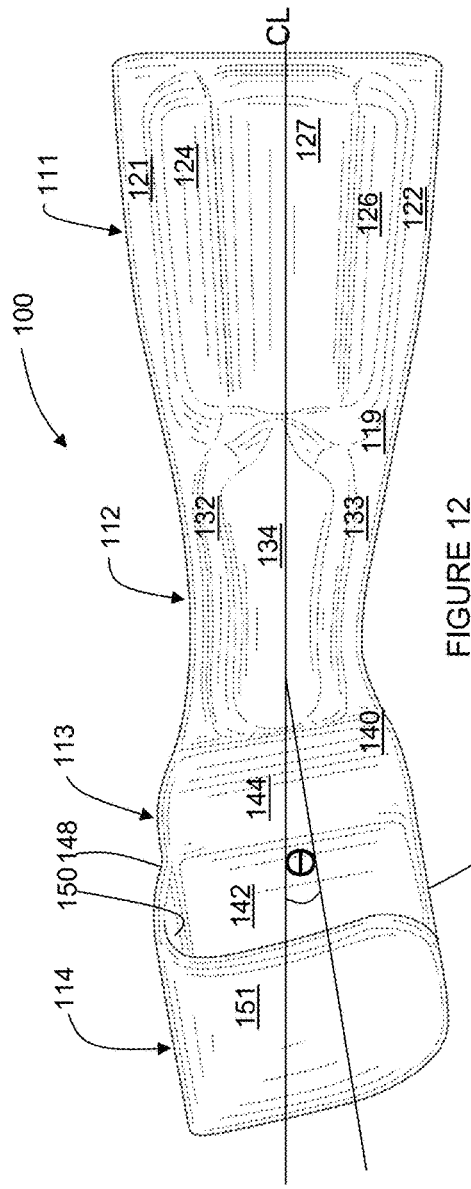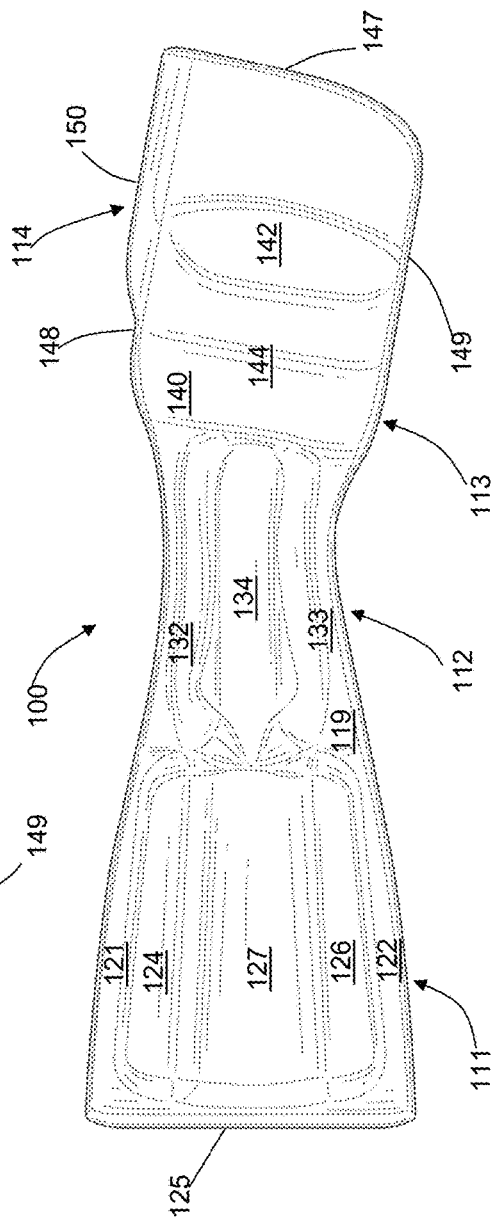
FIGURE 12
FIGURE 13

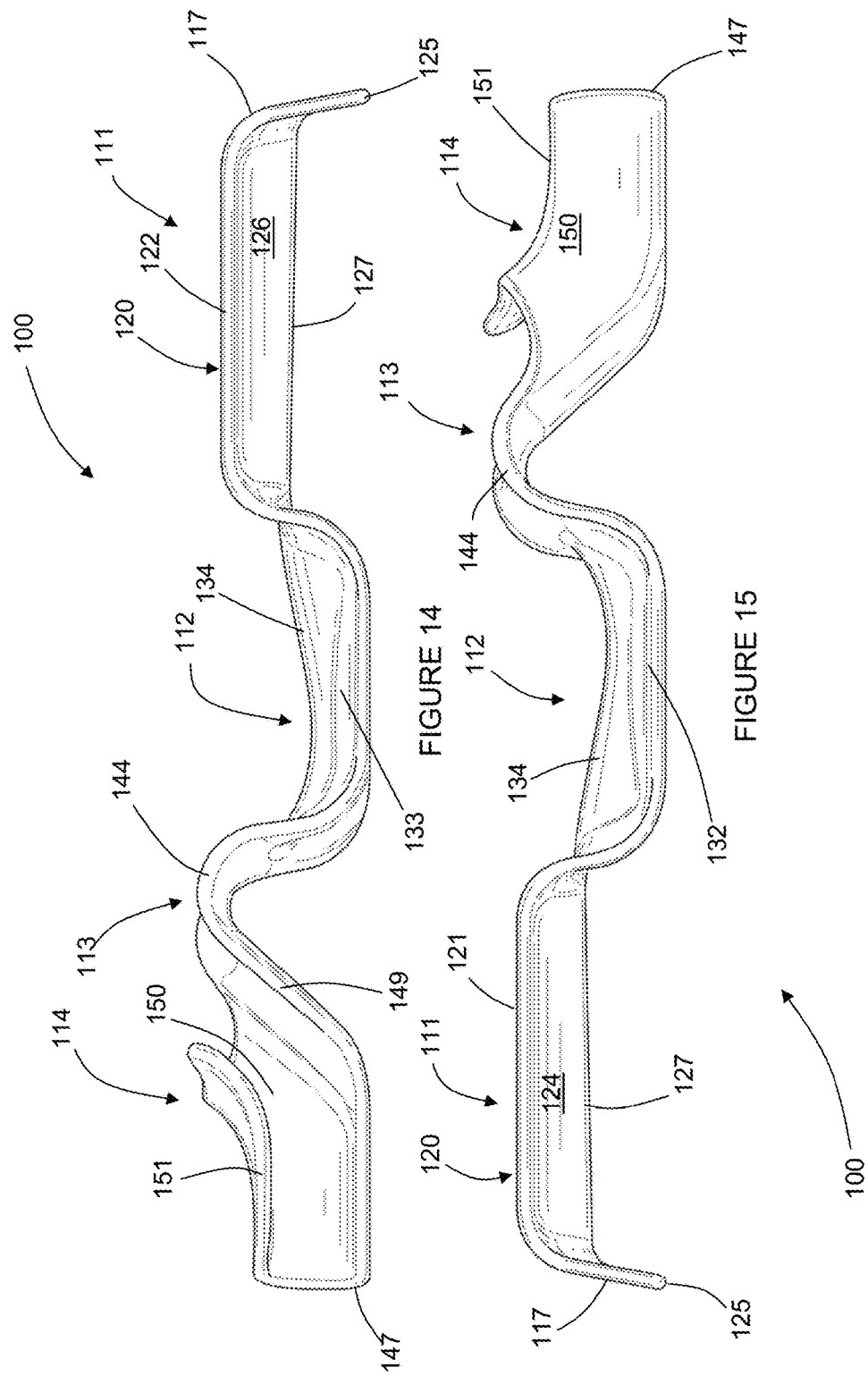

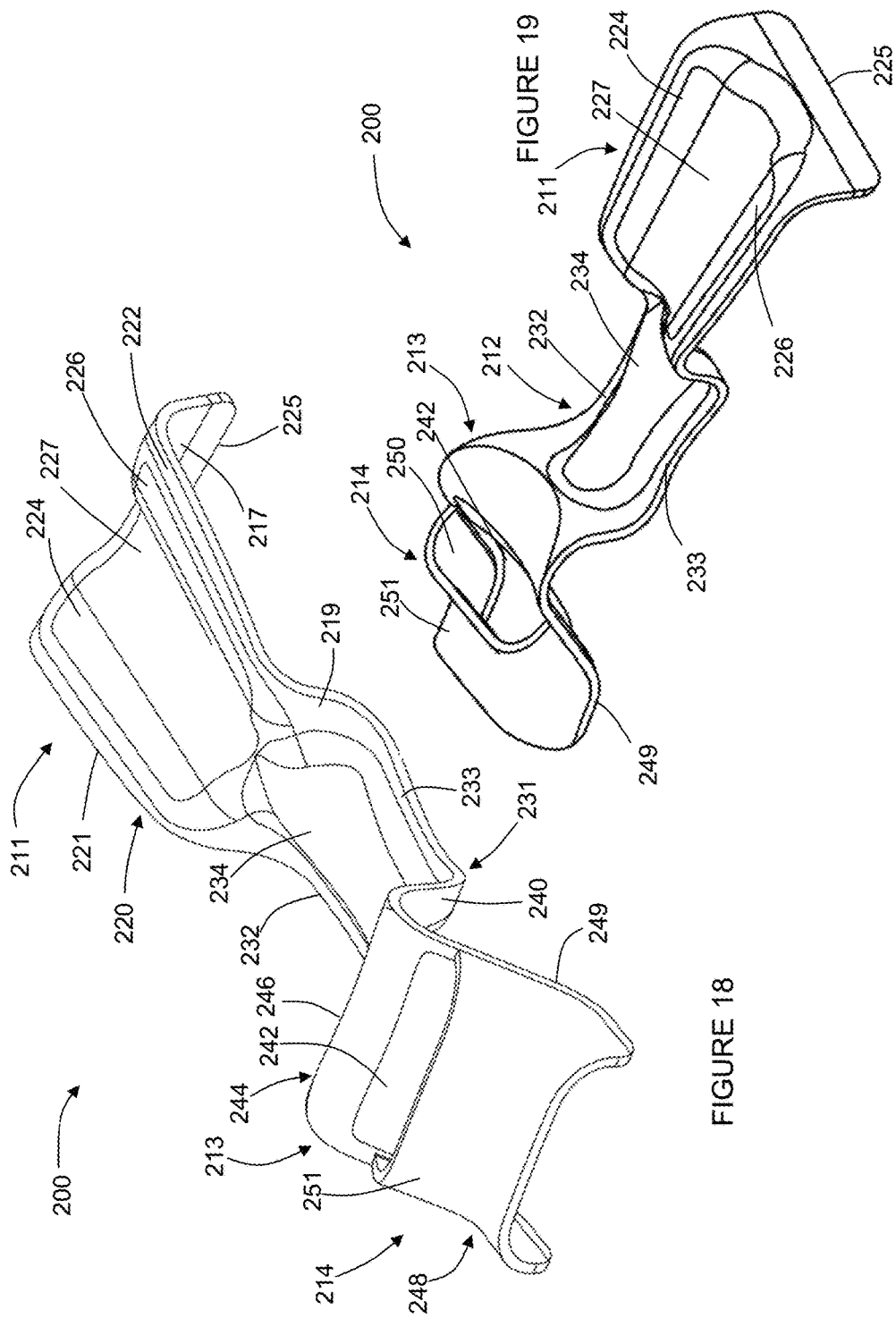

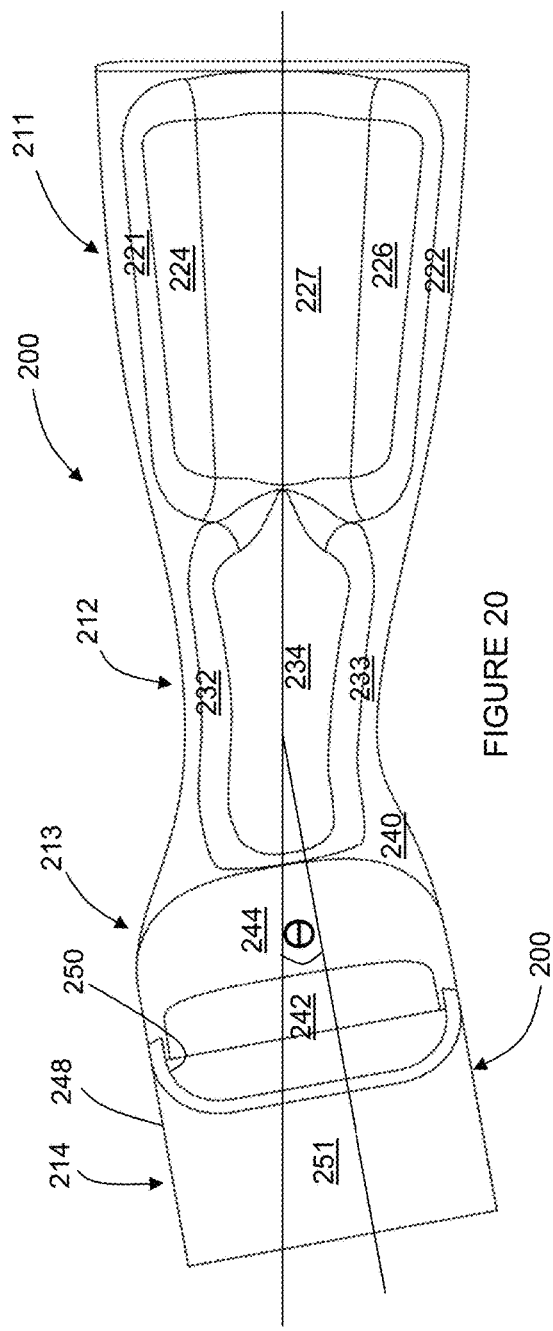
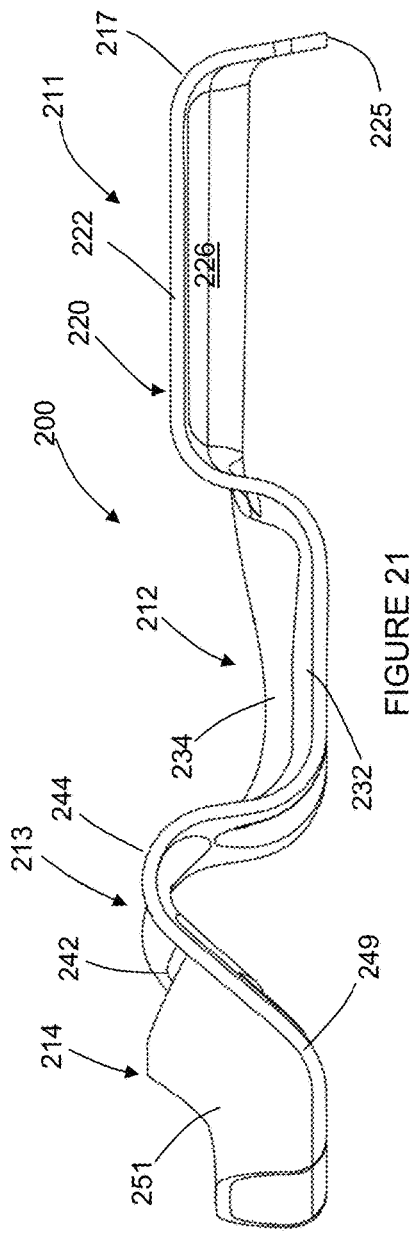
FIGURE 20
FIGURE 21

TR Band Placement

Positioning Wrist Support

OPENING ALLOWS PLACEMENT OF TR BAND

POST OP BRACE SITS UNDER ELBOW BRACE DURING PROCEDURE. THEN CAN BE EASILY SLID THROUGH FOR PLACEMENT

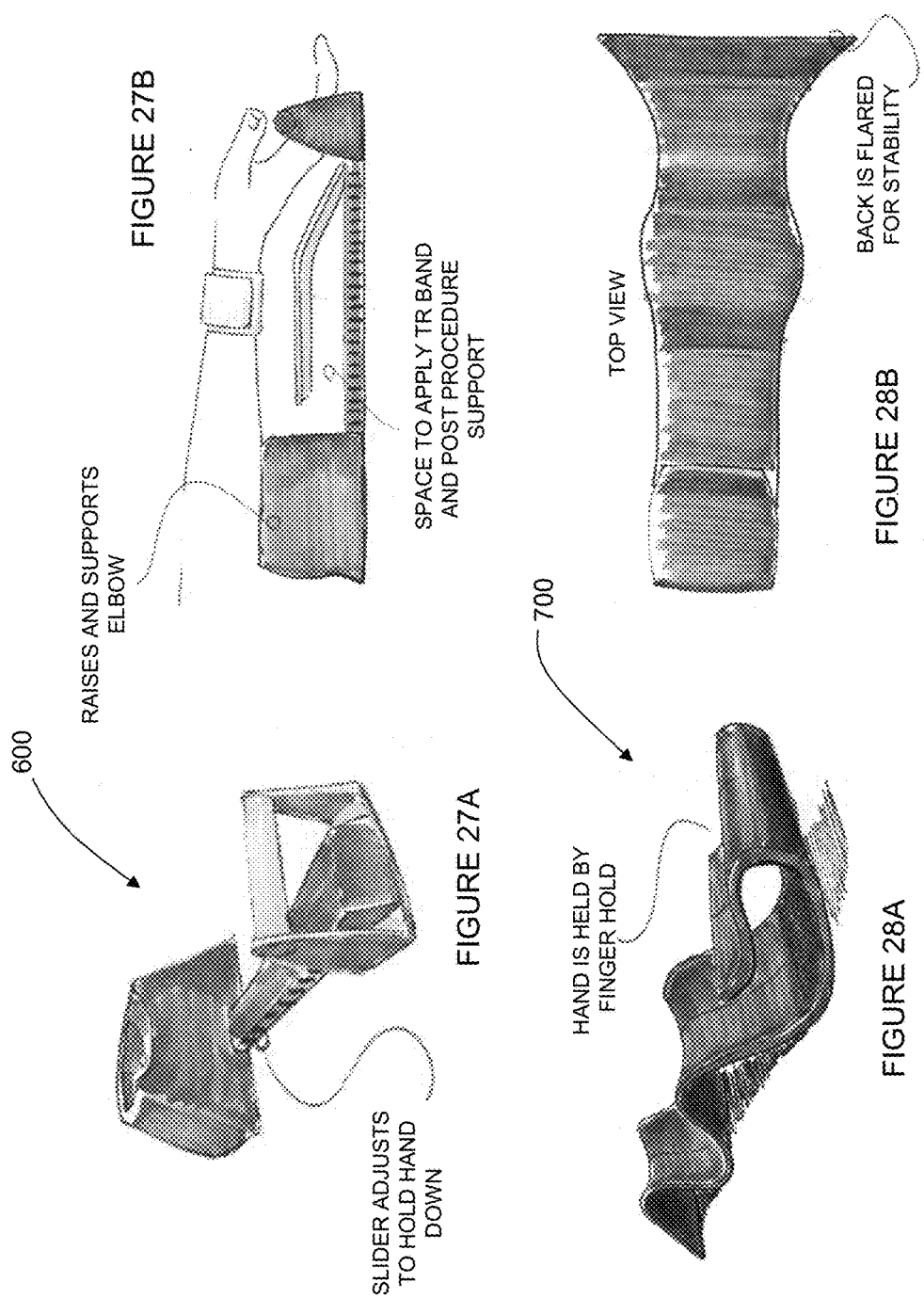

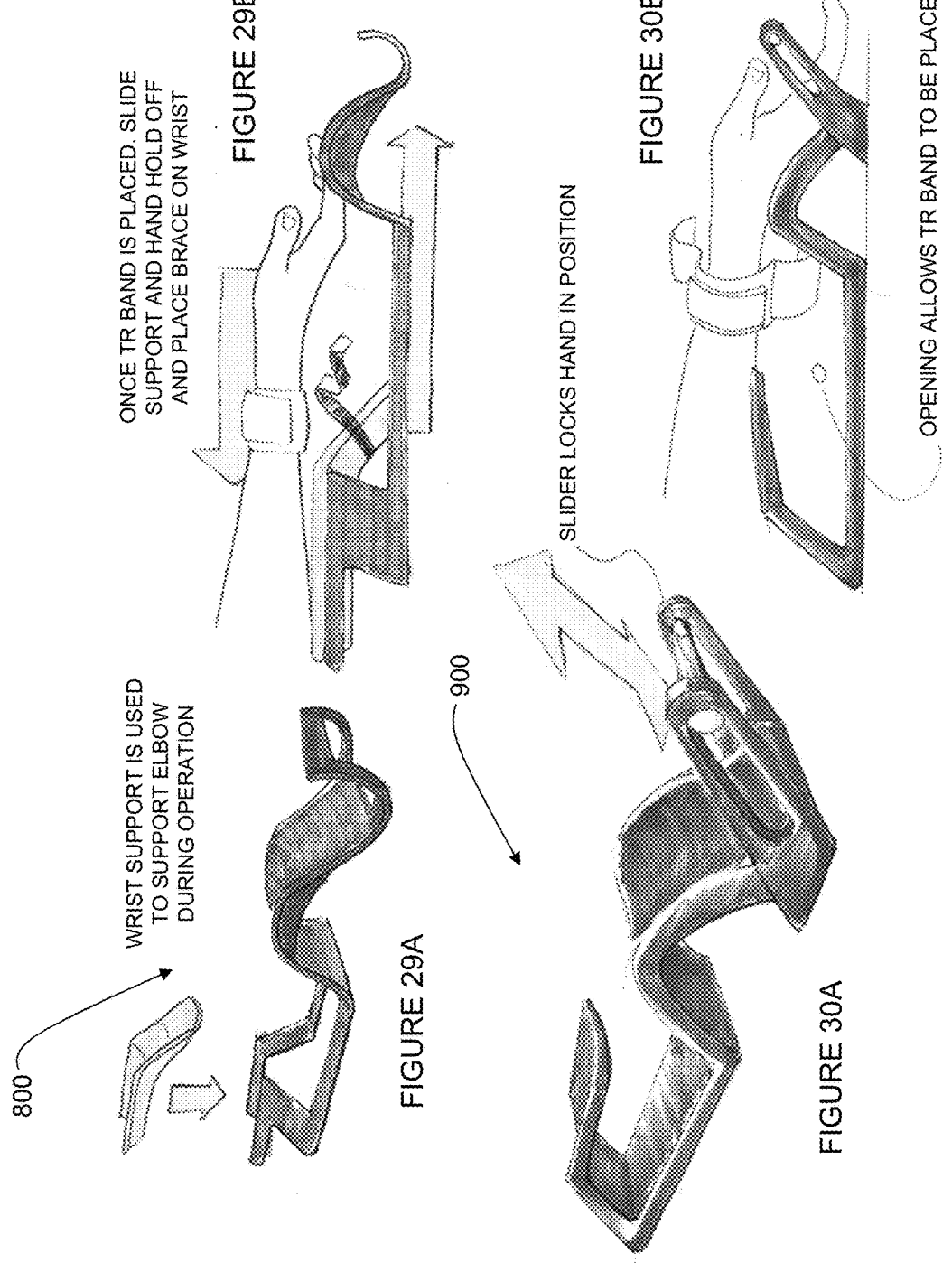

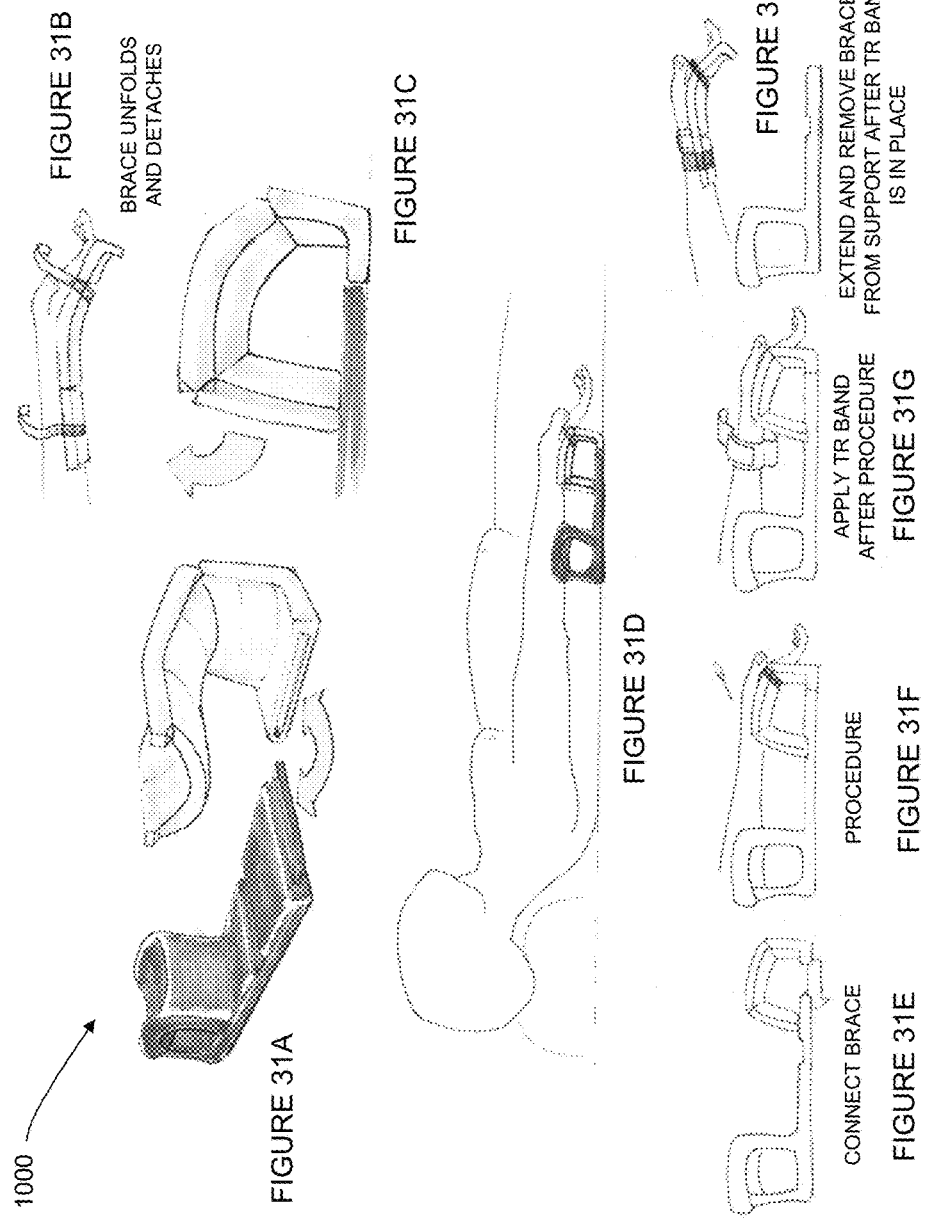

TR BAND SLIPS INTO WRIST BRACE

TR BAND TO STRAP DOWN LIKE ZIP TIE

SNAP BUTTON CONNECTS BRACE TO SUPPORT

BRACE | SUPPORT

1100

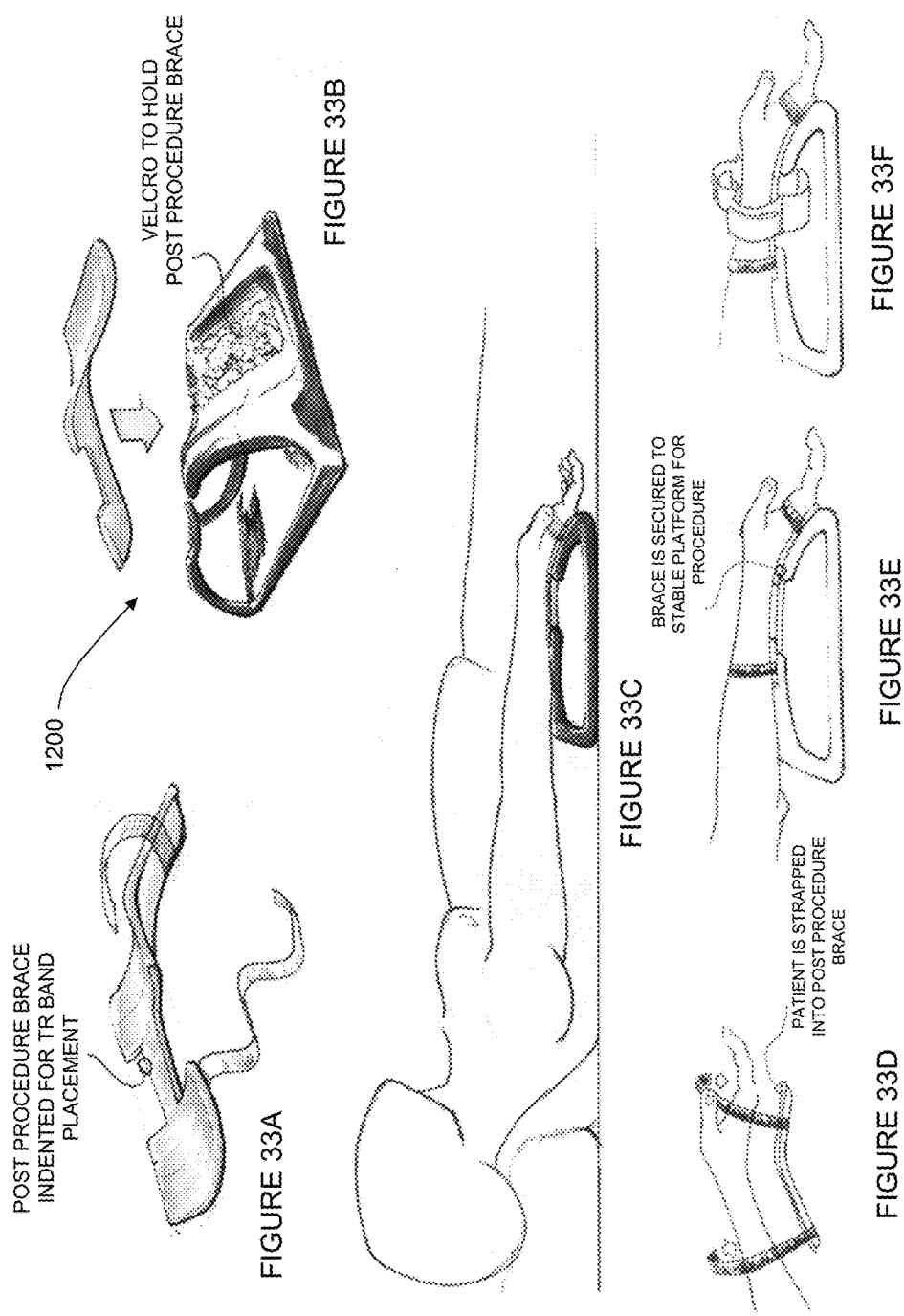

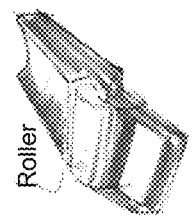 Roller Figure 34B

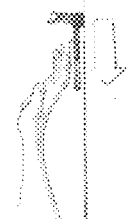
Figure 45A
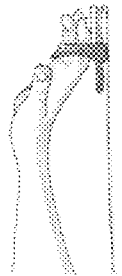
Figure 45B
Figure 49A
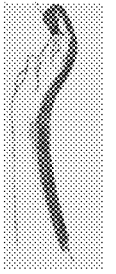
Figure 49B
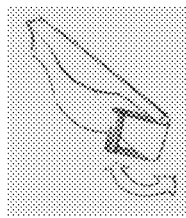
Figure 44A
Figure 44B
Figure 48A
Figure 48B
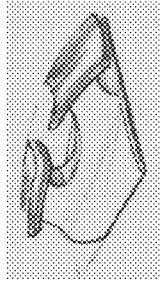
Figure 43A
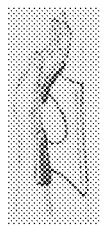
Figure 43B
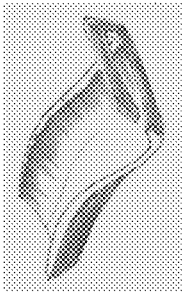
Figure 47A
Figure 47B
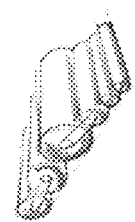
Figure 42A
Figure 42B
Figure 46A
Figure 46B

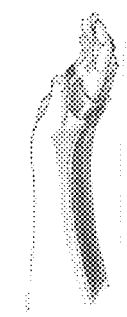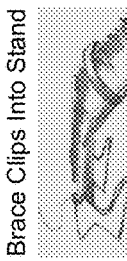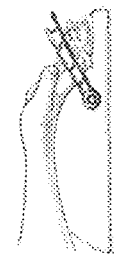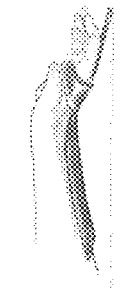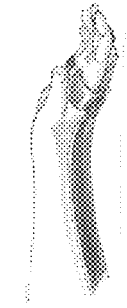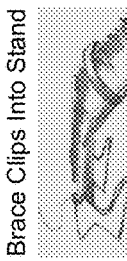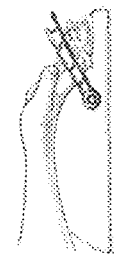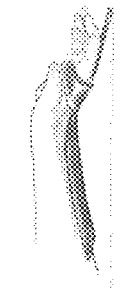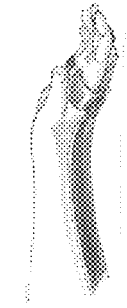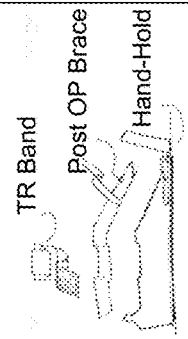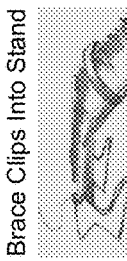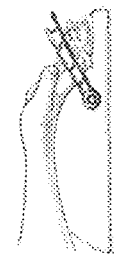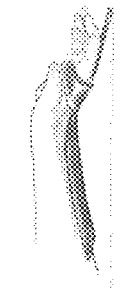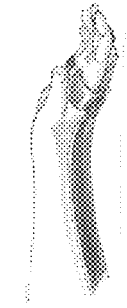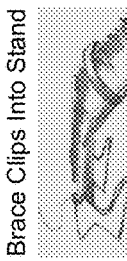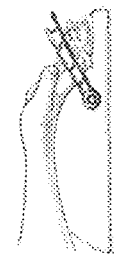

Slides Under Mattress

APPARATUS FOR SUPPORTING AN ARM DURING A MEDICAL PROCEDURE

BACKGROUND OF THE INVENTION

The present invention relates generally to an apparatus for supporting an arm, and more particularly to an apparatus for supporting an arm during medical procedures such as radial catheterization and carpal tunnel procedures.

While the apparatus may be used in various medical procedures, for clarity, the below discussion will be limited to cardiac catheterization. It should be appreciated that cardiac catheterization is being used as an example of a medical procedure only and that the apparatus may be used in other medical procedures, such as carpal tunnel procedures, that require an arm of a patient to be secured and positioned for that procedure.

Cardiac catheterization is a medical procedure used to diagnose heart conditions. The catheterization typically involves one of two types of catheterization—femoral and radial. See FIGS. 1 and 2. In general, the catheterization process uses a thin, flexible tube that is put into a blood vessel in the arm or in the groin region of a patient to allow a dye to be injected into the vessel and allow a doctor to detect blockages via an x-ray or to remove a blockage using a Coronary Stent.

In comparison to femoral catheterization, radial catheterization has a higher accidental catheter removal rate, takes about 10 minutes longer to complete, and requires a higher technical skill from the doctor; however, radial catheterization also has the benefits of the patient being able to sit up and move around immediately after the procedure, a shorter recovery time, less risk of bleeding complications, less risk of vascular complications, and seems to be preferred by both the patient and the Cardiovascular Technologist.

The radial catheterization process requires several steps. In general, they are (1) place extension board on side of x-ray table; (2) position patient on the x-ray table and prep patient; (3) clean area where the catheter is to be inserted; (4) lay down sterile towels and drape cloth over patient so that only operation site is visible; (5) numb the operation area; (6) placement of catheter; (7) inject dye into artery to check for blockages; (8) if no blockage, remove the catheter while leaving a sheath; (9) place a TR band over the artery/sheath and pump air into the TR band to apply pressure while sheath is slowly removed; (10) placing a wrist support on the patient to prevent the patient from moving their wrist; (11) remove the patient from the x-ray table and take them back to their room for one hour; (12) after one hour, nurse lets out three milliliters of air every fifteen minutes until all air is out; and (13) patient is discharged but must leave the wrist support on for 24 hours.

One of the major areas of improvement needed in the radial catheterization process is in item (2) above. In particular, the step of prepping the patient requires the patients arm to be properly positioned for insertion of the catheter. The arm support system currently used is expensive and has to be thrown away after each use, is not very stable and often cumbersome, and requires the patients hand to be taped down to secure it to the support, resulting in a less than ideal situation that is very inefficient.

More particularly, the current arm support system uses a foam pad about four inches thick that is placed on the extension board to keep the patient's arm at a level even with his/her body. A towel is rolled up and placed under the patient's wrist to flex the wrist and the patient's hand is then taped down.

Accordingly, an apparatus for supporting an arm during a medical procedure, such as radial catheterization, that improves efficiency and stability of the arm is needed.

BRIEF SUMMARY OF THE INVENTION

These and other shortcomings of the prior art are addressed by the present invention, which provides an apparatus for supporting an arm during a radial catheterization procedure to optimize the heart catheterization process by aiding in the insertion of the catheter into the artery and, thereby making the radial catheterization procedure more efficient.

According to one aspect of the invention, an apparatus configured to support an arm during a medical procedure includes an arm support section configured to support an arm of a patient, an intermediary valley section connected to a second end of the arm support section, a wrist flexing section connected to a second end of the intermediary valley section and configured to promote a downward flexing of the wrist, and a hand-hold section connected to the wrist flexing section. The hand-hold section configured to hold the wrist in the downward flexing position.

According to another aspect of the invention, an apparatus configured to support an arm during a medical procedure includes an arm support section configured to support an arm of a patient, a wrist flexing section connected to the arm support section by an intermediary valley section, and a hand-hold section connected to at least one side of the wrist flexing section and configured to hold the wrist in a downward flexing position. A portion of the arm support section and a portion of the wrist flexing section are elevated to create a space between the intermediary valley section and a forearm of a patient and to allow the patient's wrist to flex downwardly.

According to another aspect of the invention, a method for securing a patient's arm in position for a medical procedure includes the steps of providing an apparatus having an arm support section and a wrist flexing section. The method further includes the steps of placing the patient's arm on the apparatus such that a portion of the patient's arm rests on the arm support section, flexing the patient's wrist downwardly and sliding the patient's hand under a hand-hold section extending from at least one side of the wrist flexing section, and securing the patient's hand, thereby securing the patient's wrist in a downwardly extending position.

BRIEF DESCRIPTION OF THE DRAWINGS

The subject matter that is regarded as the invention may be best understood by reference to the following description taken in conjunction with the accompanying drawing figures in which:

FIG. 5 is a top view of the apparatus of FIG. 3;

FIG. 6 is a bottom view of the apparatus of FIG. 3;

FIG. 12 is a top view of the apparatus of FIG. 11;
FIG. 13 is a bottom view of the apparatus of FIG. 11;
FIG. 14 is a right side view of the apparatus of FIG. 11;
FIG. 15 is a left side view of the apparatus of FIG. 11;
FIG. 18 is a top perspective view of an apparatus according to an embodiment of the invention;
FIG. 19 is another top perspective view of the apparatus of FIG. 18;
FIG. 20 is a top view of the apparatus of FIG. 18;
FIG. 21 is a side view of the apparatus of FIG. 18;
FIGS. 26A-26F show an arm support according to an embodiment of the invention;
FIGS. 27A-27B show an arm support according to an embodiment of the invention;
FIGS. 28A-28B show an arm support according to an embodiment of the invention;
FIGS. 29A-29B show an arm support according to an embodiment of the invention;
FIGS. 30A-30B show an arm support according to an embodiment of the invention;
FIGS. 31A-31H show an arm support according to an embodiment of the invention;
FIGS. 33A-33F show an arm support according to an embodiment of the invention;
FIGS. 34A-63 show various arm supports according to embodiments of the invention.

DETAILED DESCRIPTION OF THE INVENTION

Figure 1:
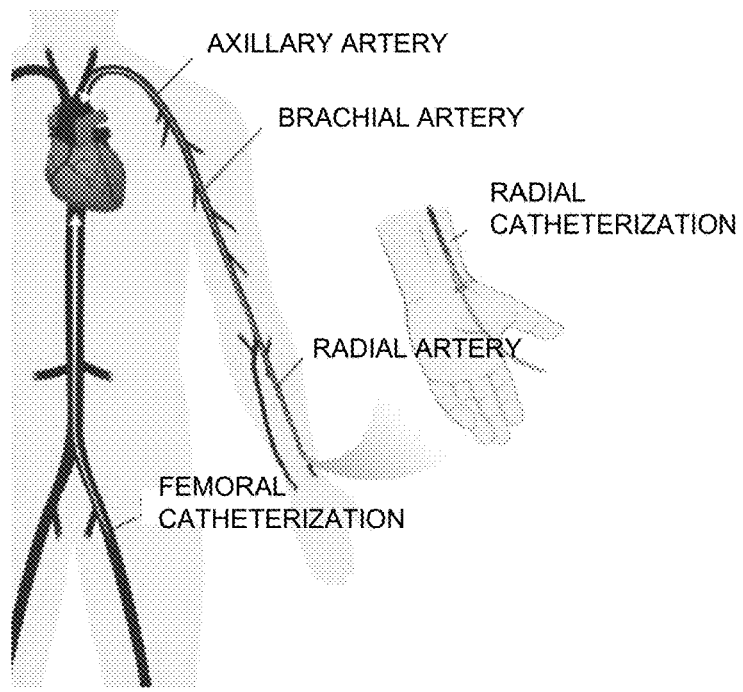
FIGS. 1 and 2 illustrate radial and femoral catheterizations.
Figure 2:
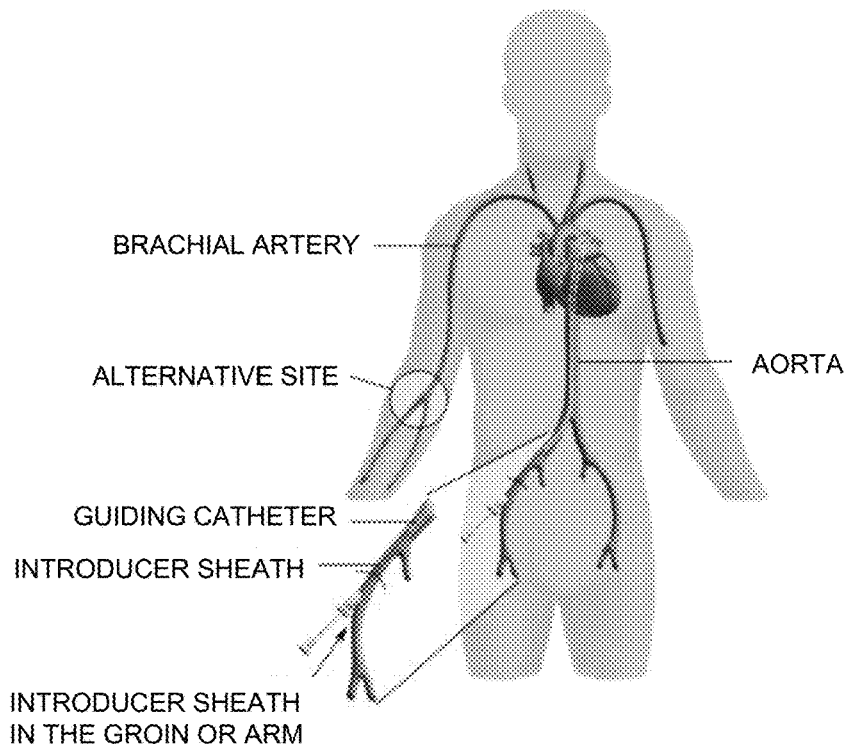

Referring to the drawings, an exemplary apparatus according to the present invention is illustrated in FIGS. 3-10 and shown generally at reference numeral 10. As shown, the apparatus 10 is of a one-piece construction and includes an arm support section 11, an intermediary valley section 12, a wrist flexing section 13, and a hand-hold section 14 to secure a patient's hand in position. As illustrated, the valley section 12 interconnects the arm support section 11 with the wrist flexing section 13. In addition, the arm support section 11 and wrist flexing section 13 are elevated from the valley section 12 to promote proper alignment of the patient's arm and to allow a radial compressive device, such as a TR Band, to be placed around the patient's arm once the catheter has been removed. While the apparatus 10 is formed of a reusable plastic, it should be appreciated that other reusable materials suitable for use in a hospital may be used.

The arm support section 11 includes a first end 16 having a downwardly extending tang 17 designed to elevate and stabilize the arm support section 11 and a second end 18 having a downwardly extending portion 19 that integrates into the valley section 12. A top surface 20, positioned between the first and second ends 16 and 18, of the arm support section 11 includes first and second 21, 22 substantially planar sections interconnected by a middle section 23.

The arm support section 11 has a length suitable to accommodate different lengths of arms such that a smaller arm may have the elbow resting towards the second end 18 and a longer arm may have the elbow resting towards the first end 16.

Figure 3:
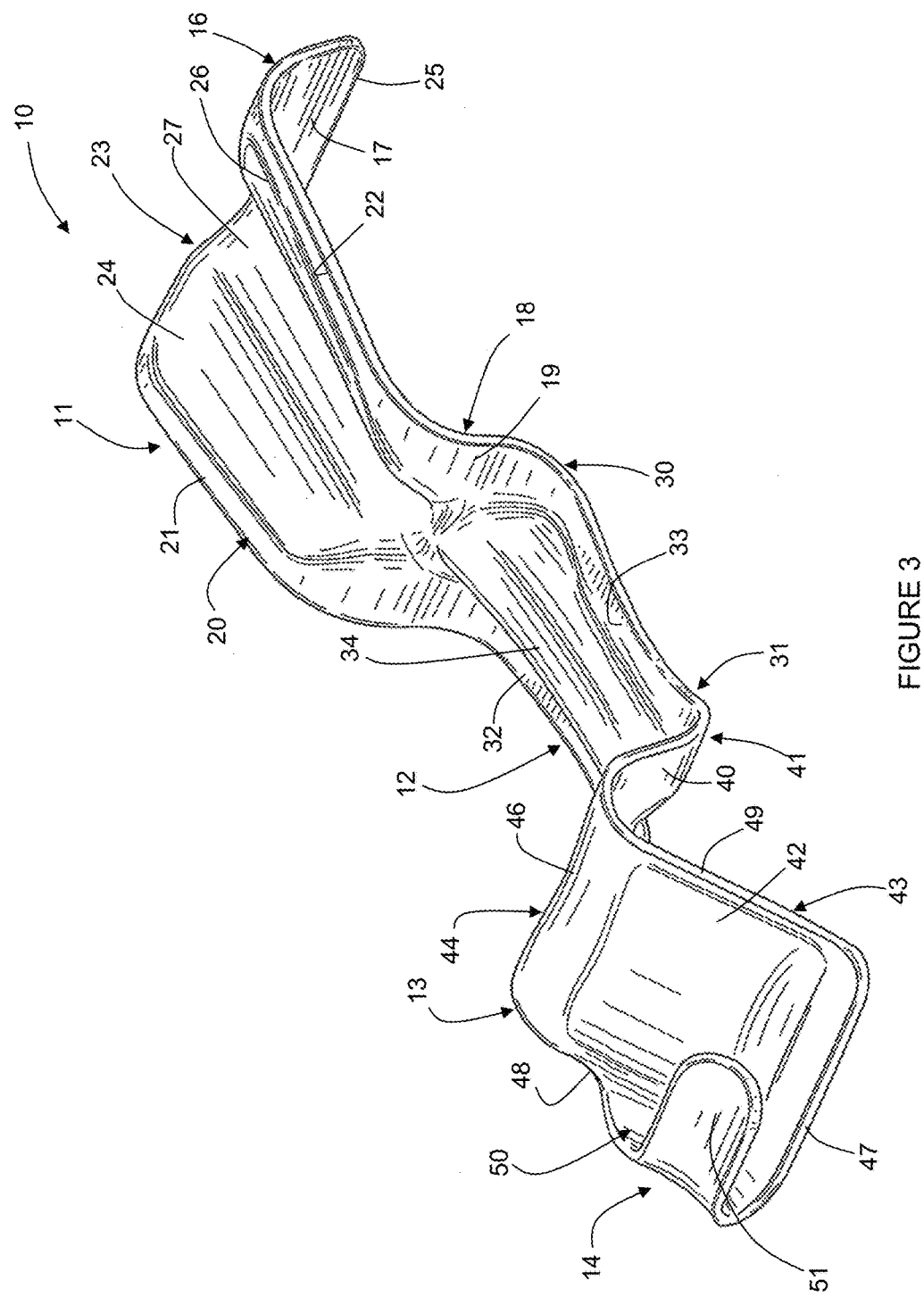
FIG. 3 is a top perspective view of an apparatus according to an embodiment of the invention.
Figure 10:
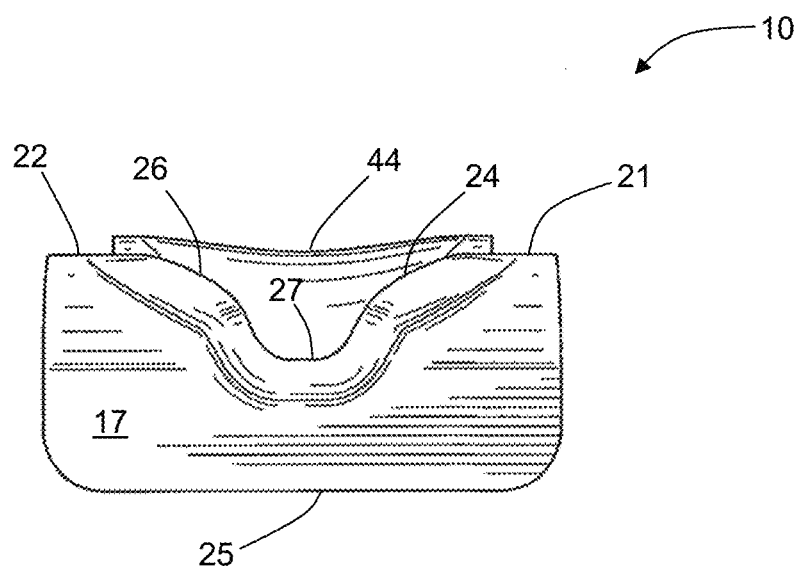
FIG. 10 is a rear view of the apparatus of FIG. 3.
Figure 11:
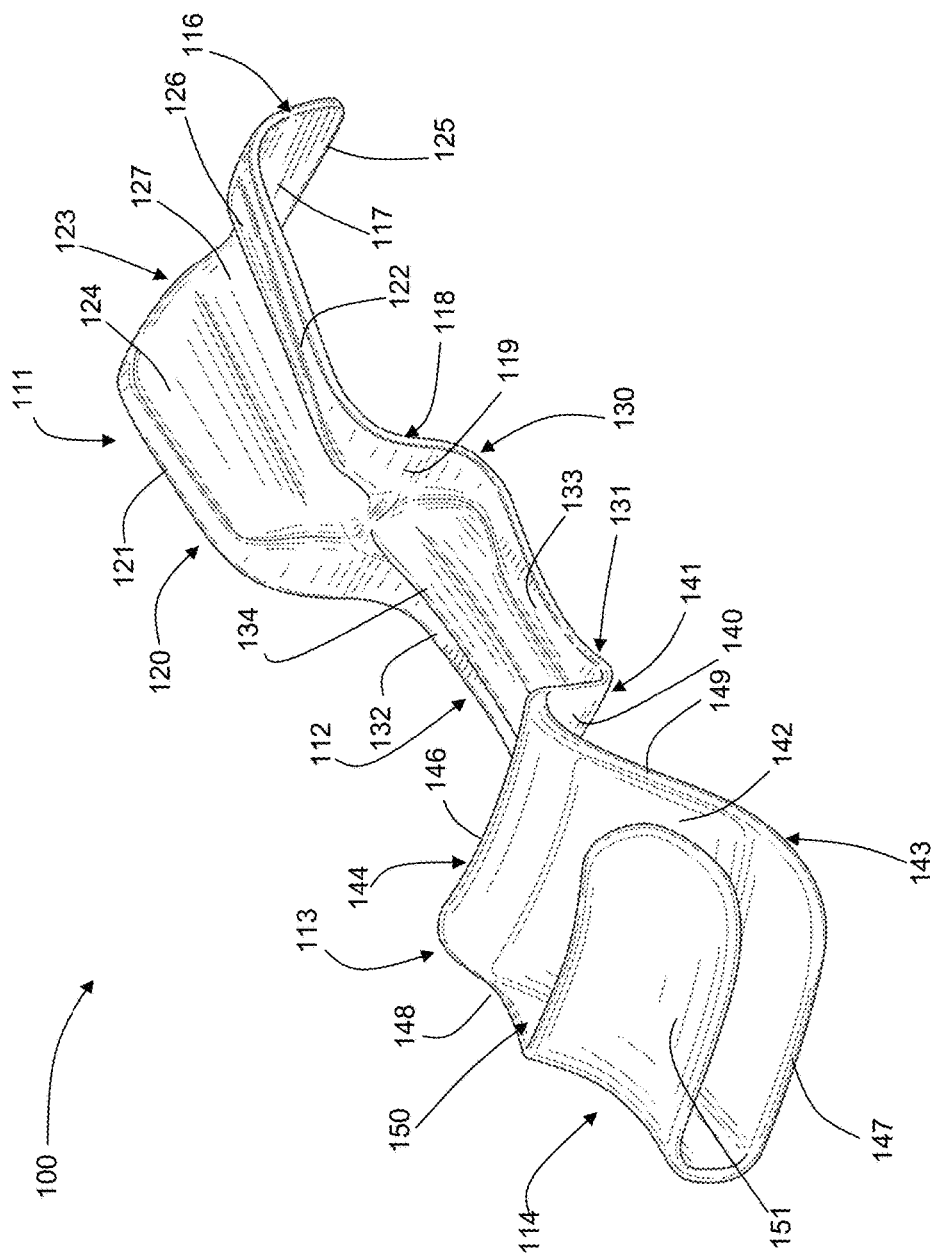
FIG. 11 is a top perspective view of an apparatus according to an embodiment of the invention.
Figure 16:
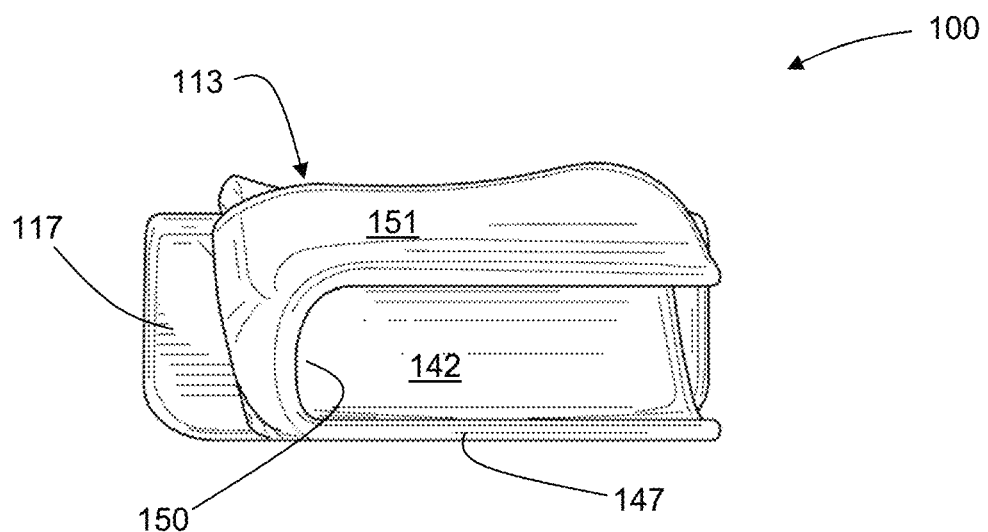
FIG. 16 is a front view of the apparatus of FIG. 11.
Figure 17:
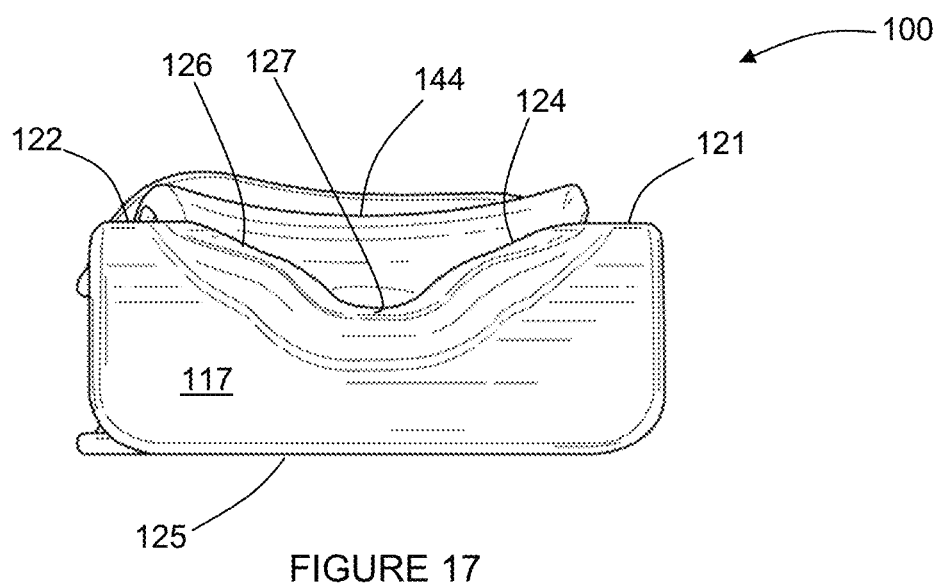
FIG. 17 is a rear view of the apparatus of FIG. 11.
Figure 22:
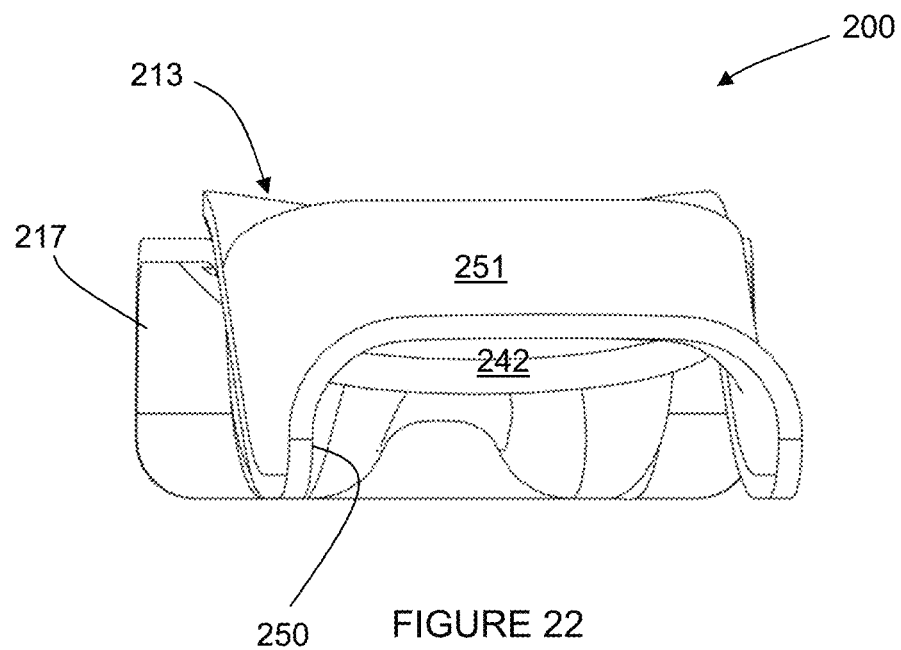
FIG. 22 is a front view of the apparatus of FIG. 18.
Figure 23:
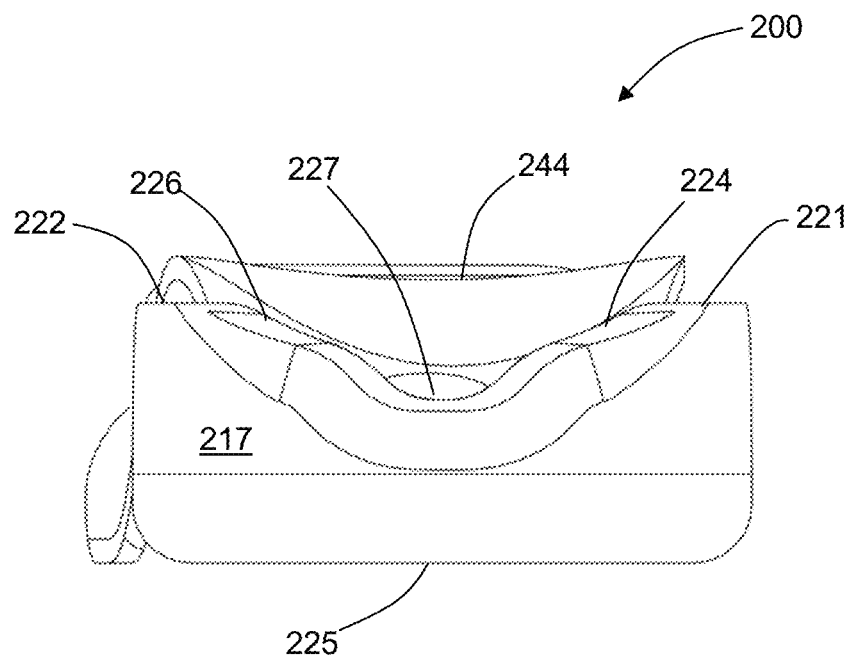
FIG. 23 is a rear view of the apparatus of FIG. 18.
Figure 24A:
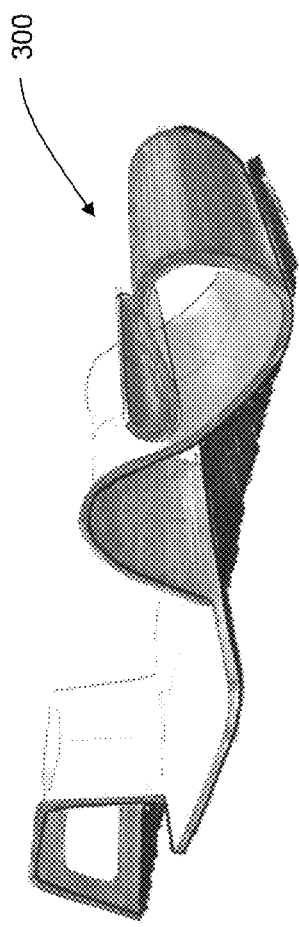
FIGS. 24A-24E show an arm support according to an embodiment of the invention.
Figures 24B, 24C:
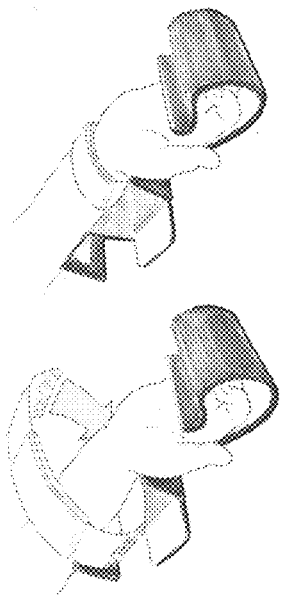
Figures 24D, 24E:
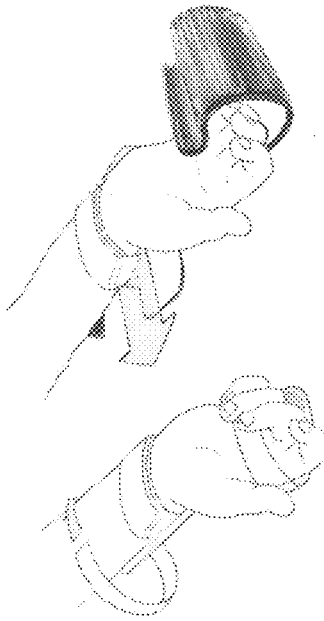
Figure 25:
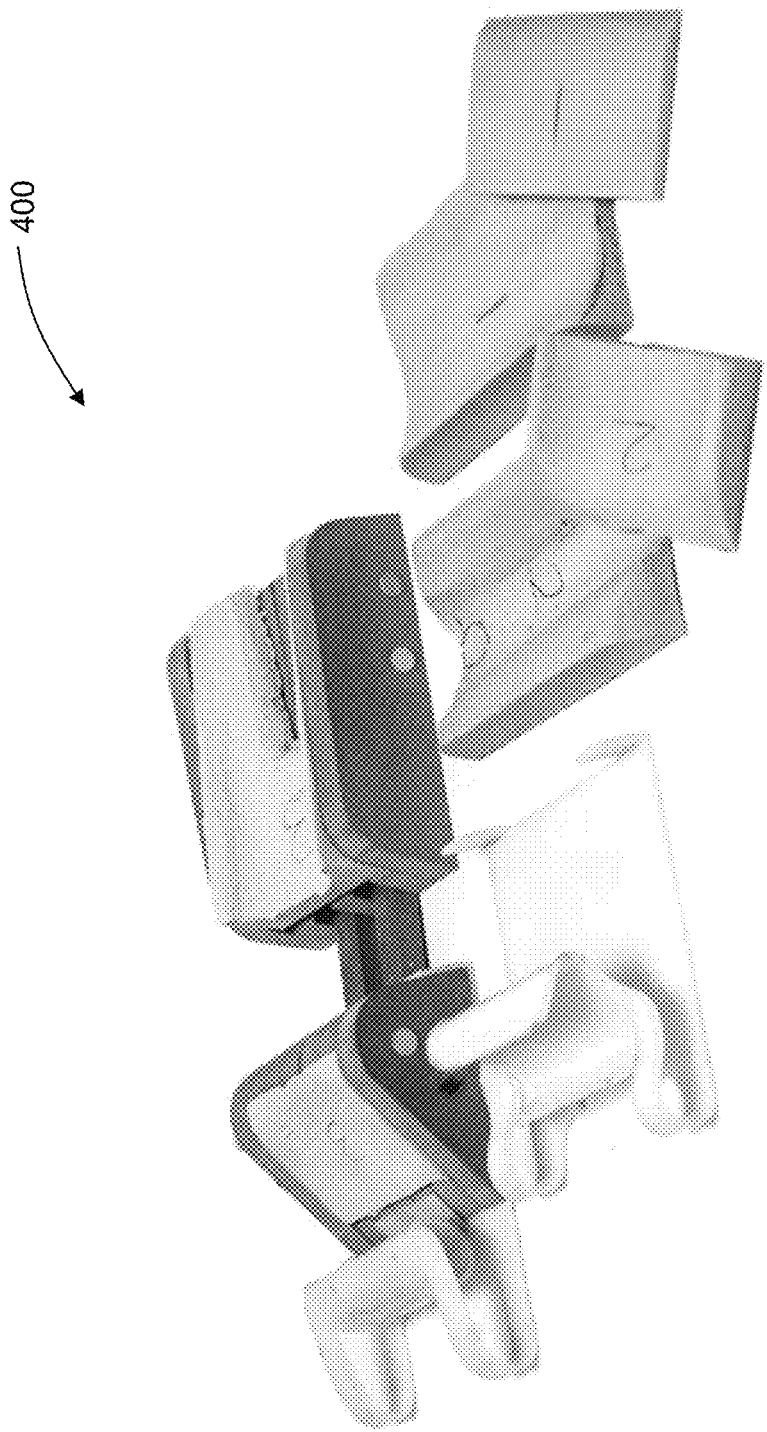
FIG. 25 shows an arm support according to an embodiment of the invention.
Figure 32B:
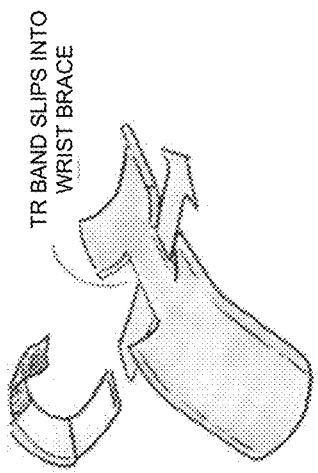
FIGS. 32A-32D show an arm support according to an embodiment of the invention.
Figure 32A:
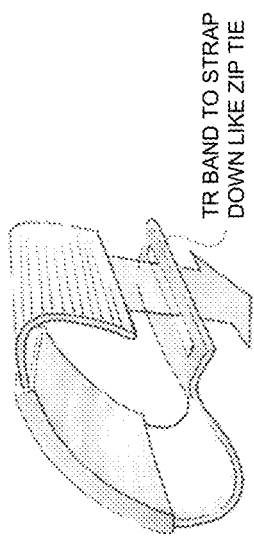
Figure 32C:
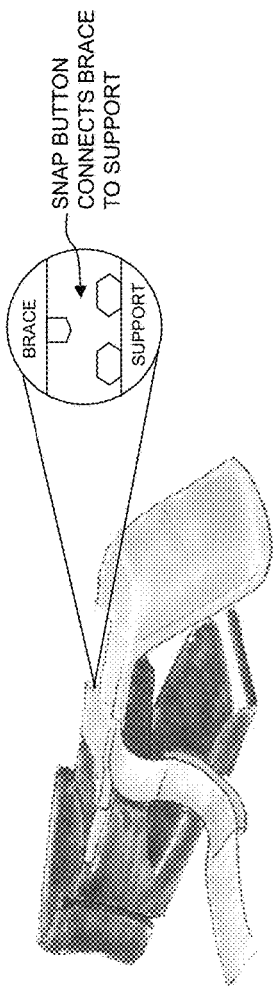
Figure 32D:
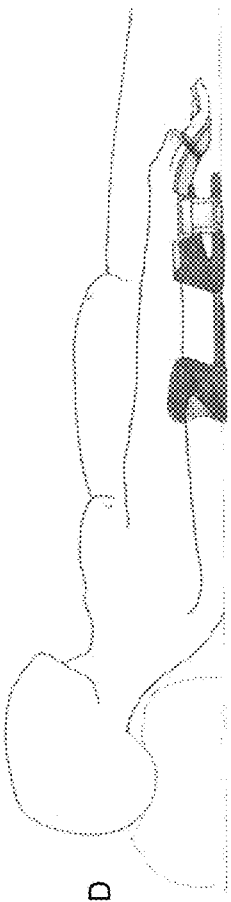
Figure 34A:
Figure 35A:
Figure 35B:
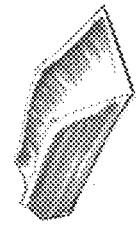
Figure 36A:
Figure 36B:
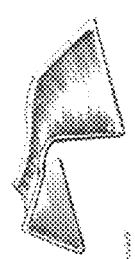
Figure 37A:
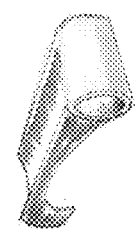
Figure 37B:

The middle section 23 is concaved to provide a stable and comfortable support for the patient's forearm and elbow. More particularly, the middle section 23 is formed by first and second sides 24 and 26 interconnected by a valley 27 that extends from the first end 16 to the second end 18. As shown in FIGS. 3, 5, and 10, side 24 slopes downwardly at a pre-determined angle from first planar section 21 towards a first top portion 28 of the valley 27 and side 26 slopes downwardly at a pre-determined angle from the second planar section 22 towards a second top portion 29 of the valley 27. It should be appreciated that the angle of slope for the sides 24 and 26 is selected to provide a stable and comfortable support for the patient's arm. For example, the apparatus 10 may come in different sizes for different sized patient's, i.e., small, medium, and large.

The valley 27 has a width suitable to accommodate a patient's elbow, such that when the patient's arm is positioned in the apparatus 10, the patient's elbow is positioned in the valley 27 to alleviate any pressure that may otherwise be created on the elbow (i.e., the sides 24 and 26 support the sides of the patient's arm and the valley 27 allows the elbow to be free or substantially free of contact by the apparatus 10).

Figure 4:
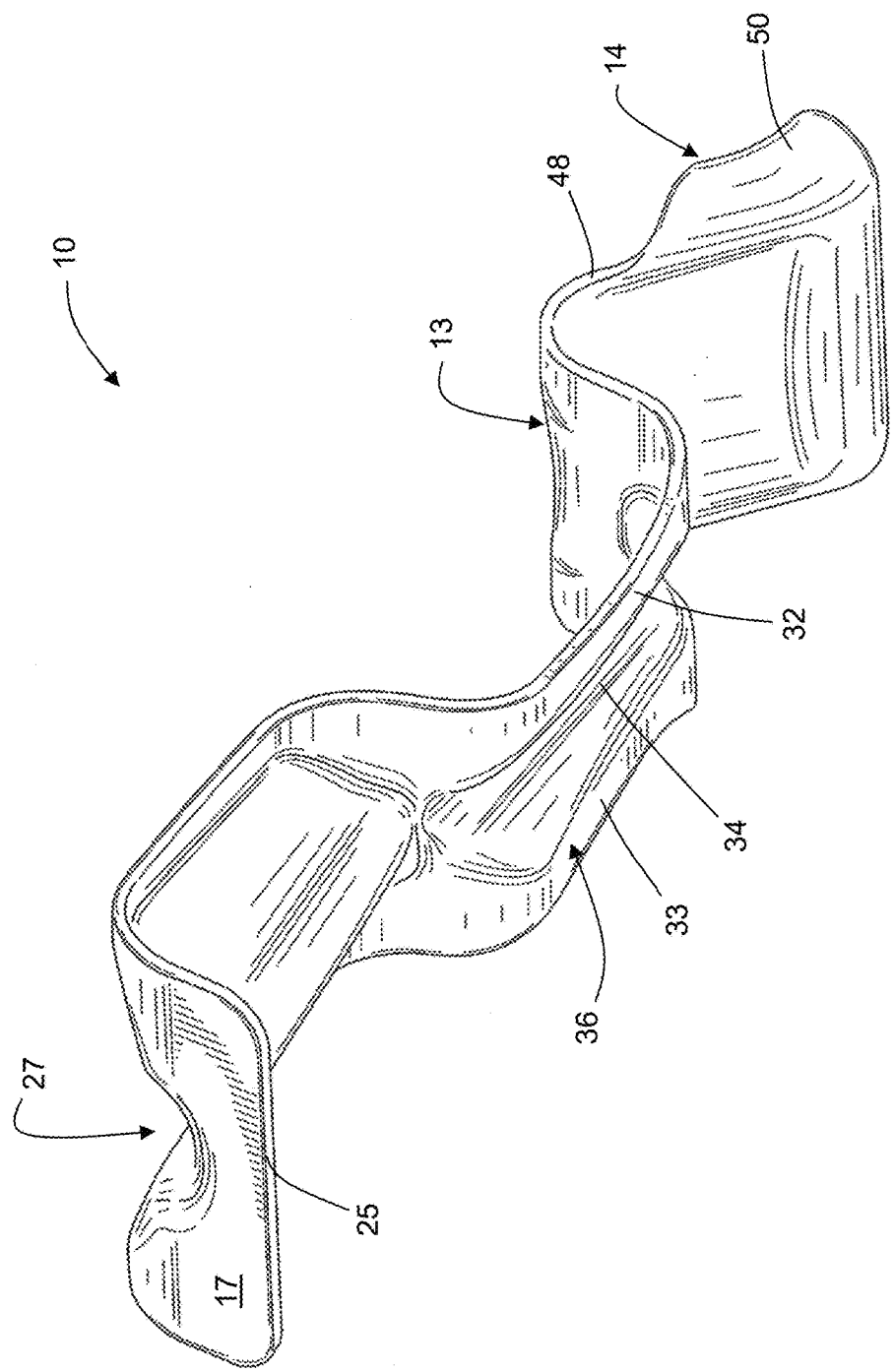
FIG. 4 shows a bottom perspective view of the apparatus of FIG. 3.
Figure 7:
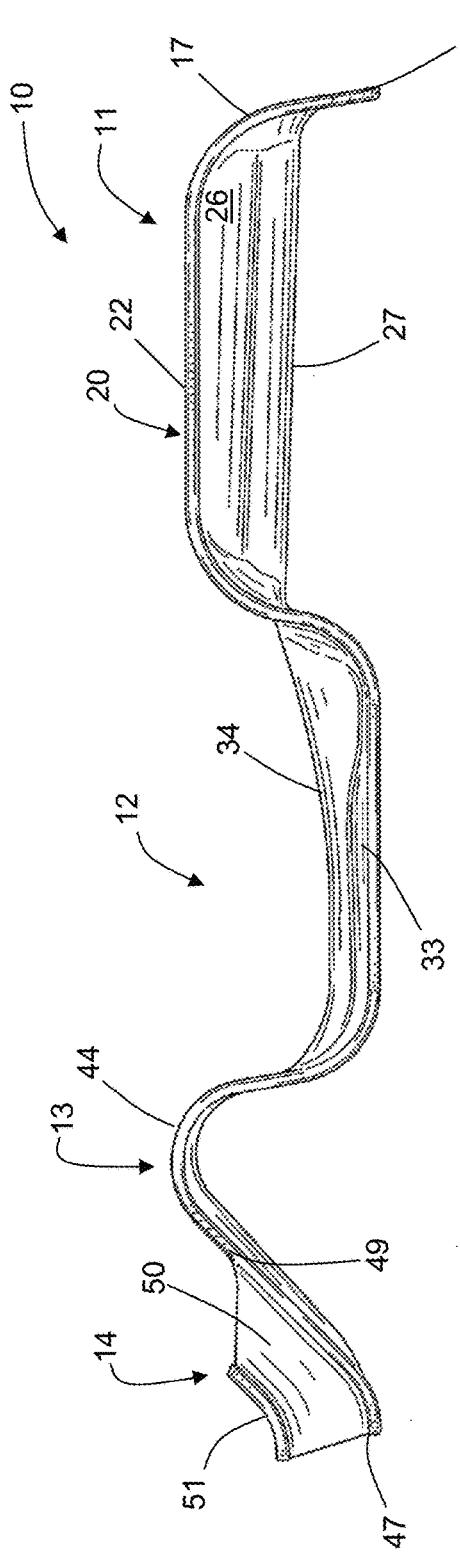
FIG. 7 is a right side view of the apparatus of FIG. 3.
Figure 8:
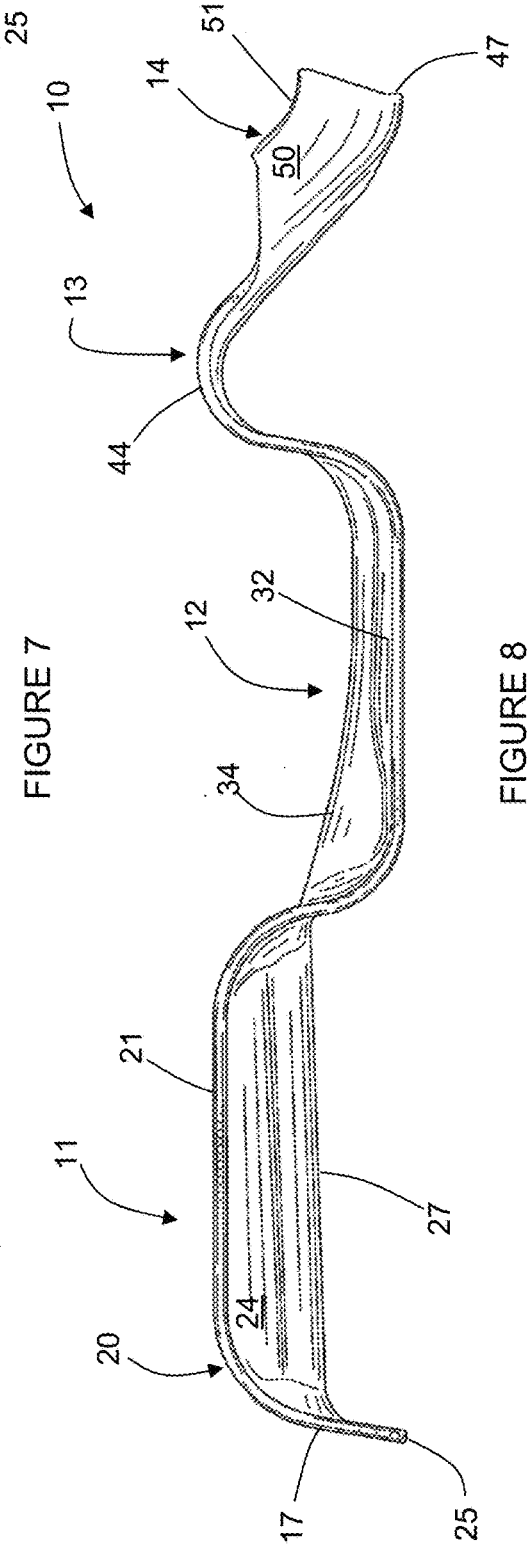
FIG. 8 is a left side view of the apparatus of FIG. 3.
Figure 9:
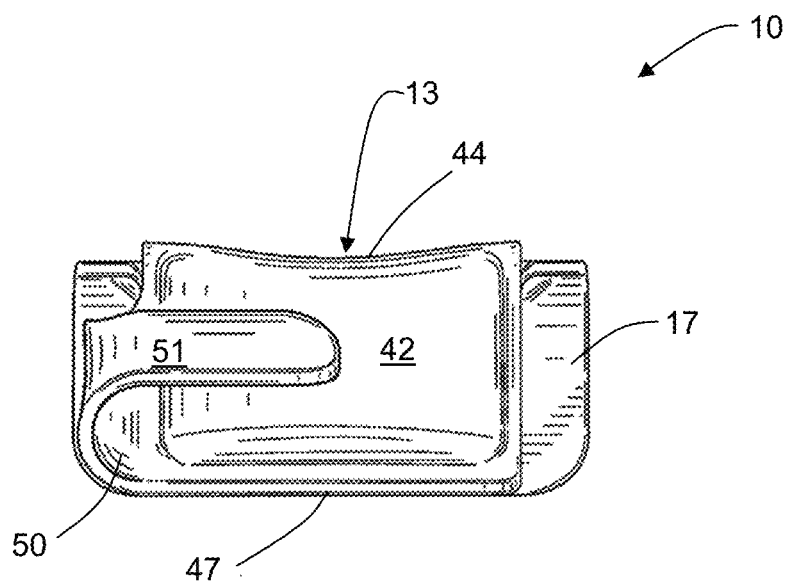
FIG. 9 is a front view of the apparatus of FIG. 3.

As discussed above, the valley section 12 interconnects the arm support section 11 and the wrist flexing section 13. A first end portion 30 of the valley section 12 is connected to the downwardly extending portion 19 of the arm support section 11 and a second end portion 31 is connected to a downwardly extending portion 40 of a first end 41 of the wrist flexing section 13. The valley section 12 includes first and second 32, 33 substantially planar sections interconnected by a middle section in the form of a tunnel 34 extending between the first end portion 30 and the second end portion 31. The tunnel 34 provides rigidity to the arm support 10 to prevent flexing and twisting. As shown in FIGS. 4 and 6, a bottom surface 36 of the first and second sections 32 and 33 is substantially planar and lies substantially in the same plane as a bottom edge 25 of the downwardly extending portion 19 to promote a stable platform to support an arm and allow the apparatus 10 to lie on a table or other substantially flat surface. See FIGS. 7 and 8.

As discussed, the wrist flexing section 13 is connected to the second end portion 31 of the valley section 12 by the downwardly extending portion 40. The wrist flexing portion further includes a downwardly extending portion 42 of a second end 43 and a raised middle section 44 interconnecting the first and second ends 41 and 43. A bottom edge 47 of the second end 43 lies substantially in the same plane as the edge 25 and bottom surface 36 to further provide stability to the apparatus 10. See FIGS. 5 and 6.

The middle section 44 is in the form of a narrow hump to allow the patient's wrist to flex downwardly and has a top surface 46 that lies substantially in the same plane as the top surface 20 of the arm support section 11 to allow the patient's arm to lie flat in the apparatus 10. See FIGS. 5 and 6. It should be appreciated that the middle section is sized to not only allow the wrist to flex downwardly, but to also provide stability and comfort to the patient.

The hand-hold section 14 extends from a side edge 48 or 49 of the downwardly extending portion 42. As shown in the Figures, the hand-hold section 14 extends from side edge 48, but it may extend from either side edge 48, 49 to accommodate right or left arm catheterization. The hand-hold section 14 is designed to allow a patient's hand to lie between the hand-hold section 14 and the downwardly-extending portion 42 of the wrist flexing section 13 and secure the hand therebetween.

As shown, the hand-hold section 14 includes a base portion 50 and a tang or handle 51 extending from the base portion 50. The base portion 50 has a curvature to position the tang 51 in a substantially parallel alignment with the downwardly extending portion 42 so that the patient's fingers can wrap around the tang 51 comfortably, thereby holding the patient's hand in position.

In use, the apparatus 10 is placed on a substantially flat surface, such as a table, along a side of the patient and at a location for use with the patient's arm. The patient's arm is then laid onto the apparatus 10 along its length, such that a portion of the patient's forearm is supported by the arm support section 11 and the patient's wrist is supported by the middle section 44 of the wrist flexing section 13. Sides of the patient's forearm are supported by sides 24 and 26 and the patient's elbow resides in the valley 27 to alleviate pressure thereon. The apparatus 10 is then adjusted along the length of the patient's arm to insure that the patient's wrist is properly aligned with and supported by the middle section 44 of the wrist flexing section 13. It should be appreciated that while the arm support section 11 has a length suitable for adjusting the arm support 10 to different sizes of arms, the arm support 10 may also be designed in different lengths, i.e., small, medium, and large, to accommodate different length arms.

Once the apparatus 10 has been adjusted, the patient's hand is slid between the downwardly extending portion 42 of the wrist flexing section 13 and the hand-hold section 14 so that the patient can wrap his/her fingers around the tang 51 of the hand-hold section 14, thereby flexing and securing the wrist in a downwardly position to allow insertion of the catheter. Once the catheter procedure is finished, the catheter is removed and a TR Band is slid through a space created between the patient's arm and the valley section 12 of the apparatus 10 and then wrapped around the patient's arm. The space is created by the difference in elevation between the valley section 12 and the arm support 11 and the wrist flexing sections 13. With the TR Band in place, a temporary post-op support may be slid into the space between the arm and valley section 12 to maintain proper alignment of the wrist for 24 hours or the apparatus 10 may be maintained on the patient's arm by a wrap for the 24 hour post-op period.

Referring now to FIGS. 11-17, an apparatus according to an embodiment of the invention is shown generally at reference numeral 100. Like apparatus 10, apparatus 100 includes an arm support section 111, an intermediary valley section 112, a wrist flexing section 113, and a hand-hold section 114 to secure a patient's hand in position. It should be appreciated that like numbers represent like elements. The arm support section includes a downwardly extending tang 117, a downwardly extending portion 119, a top surface 120, a middle section 123, and a valley 127. The intermediary valley section 112 includes first and second 132, 133 substantially planar sections interconnected by a tunnel 134. The wrist flexing section 113 includes a downwardly extending portion 142 and a raised middle section 144 in the form of a narrow hump to allow a patient's wrist to flex. The hand-hold section 114 includes a base portion 150 and a tang 151 for the patient's fingers to wrap around.

Unlike apparatus 10, as shown in FIG. 12, apparatus 100 includes a bend or offset θ of about five (5) to about (20) degrees from a centerline of the apparatus 100. Preferably, the offset is about ten (10) degrees. The offset provides a greater degree of comfort to the patient and allows greater flexibility in performing the procedure.

Referring now to FIGS. 18-23, an apparatus according to an embodiment of the invention is shown generally at reference numeral 200. It should be appreciated that like numbers represent like elements. Like apparatuses 10 and 100, apparatus 200 includes an arm support section 211, an intermediary valley section 212, a wrist flexing section 213, and a hand-hold section 214 to secure a patient's hand in position. It should be appreciated that like numbers represent like elements. The arm support section includes a downwardly extending tang 217, a downwardly extending portion 219, a top surface 220, a middle section 223, and a valley 227. The intermediary valley section 212 includes first and second 232, 233 substantially planar sections interconnected by a tunnel 234. The wrist flexing section 213 includes a downwardly extending portion 242 and a raised middle section 244 in the form of a narrow hump to allow a patient's wrist to flex.

Additionally, like apparatus 100, apparatus 200 includes an offset θ of about five (5) to about twenty (20) degrees. Preferably the offset is about ten (10) degrees. Unlike apparatuses 10 and 100, the hand-hold section 214 a full-length handle 251 that is connected at a first end 250 to side edge 248 and at a second end 260 to side edge 249 of the downwardly extending portion 242. Thus, unlike hand-hold section 114, the handle 251 extends from side edge 248 to side edge 249 to provide a pocket between the handle 251 and the downwardly extending portion 242 for a patient's hand to slide into.

Referring to FIGS. 24A-33F, it should be appreciated that varying embodiments of the apparatuses 10, 100, and 200 may be used. For example, the hand-hold section may extend from the bottom edge of the wrist flexing section to allow the arm support to be used in both right and left arms, FIGS. 24A-24E (shown generally at reference numeral 300) and FIGS. 28A-28B (shown generally at reference numeral 700). The arm support may be formed of multiple sections to allow for adjustment of the length and of the padding contour used, FIG. 25 (shown generally at reference numeral 400). The wrist flexing section may be removed altogether such that the flexing of the wrist is created by the angle of the hand-hold section and arm support section, FIGS. 26A-26F (shown generally at reference numeral 500) and FIGS. 27A-27B (shown generally at reference numeral 600). The post-op wrist support may be incorporated into the arm support by using it as the arm support section, FIGS. 29A-29B (shown generally at reference numeral 800), or as the wrist flexing section, FIGS. 31A-31H (shown generally at reference numeral 1000), or as the wrist flexing section with a provision for incorporating a TR Band, FIGS. 32A-32D (shown generally at reference numeral 1100). A slider bar may be used for the hand-hold section to lock the hand in position, FIGS. 30A-30B (shown generally at reference numeral 900). Additionally, the arm support may be designed with Velcro positioned on the wrist flexing section to secure a post-op wrist support thereto, FIGS. 33A-33F (shown generally at reference number 1200).

Figure 38A:
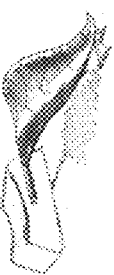
Figure 38B:
Figure 39A:
Figure 39B:
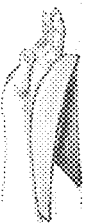
Figure 40A:
Figure 40B:
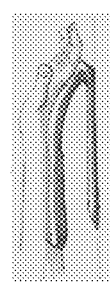
Figure 41A:
Figure 41B:
Figure 59:
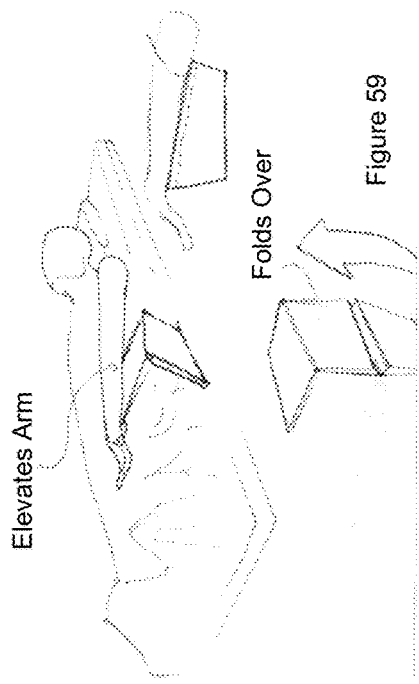
Figure 61:
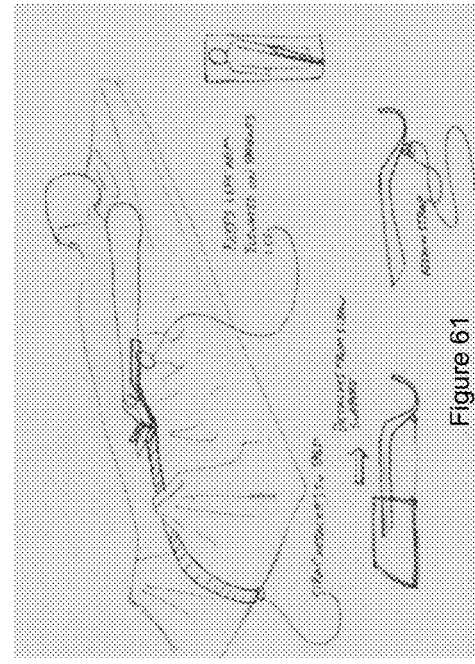
Figure 58:
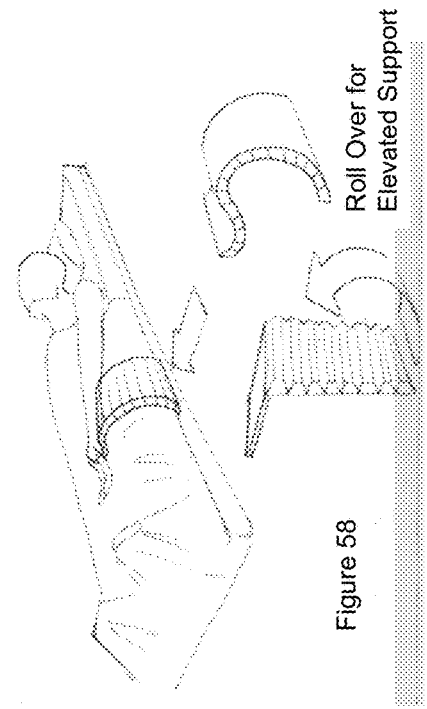
Figure 60:
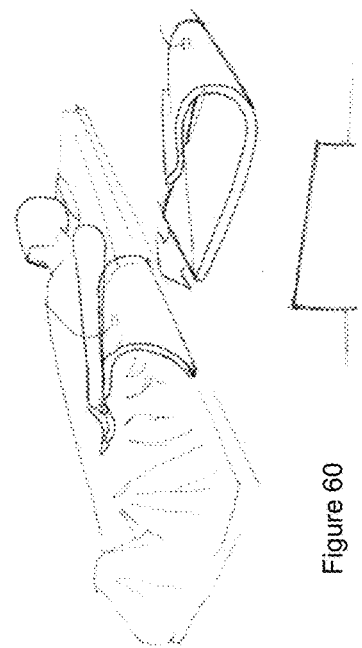
Figure 63:
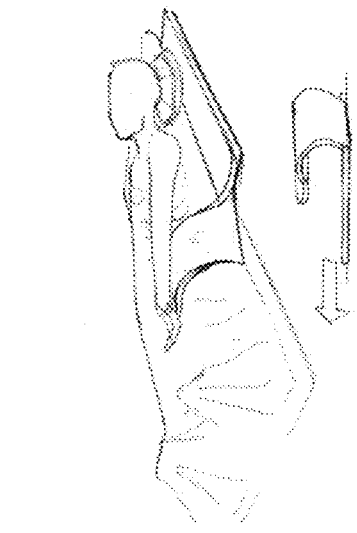
Figure 62:
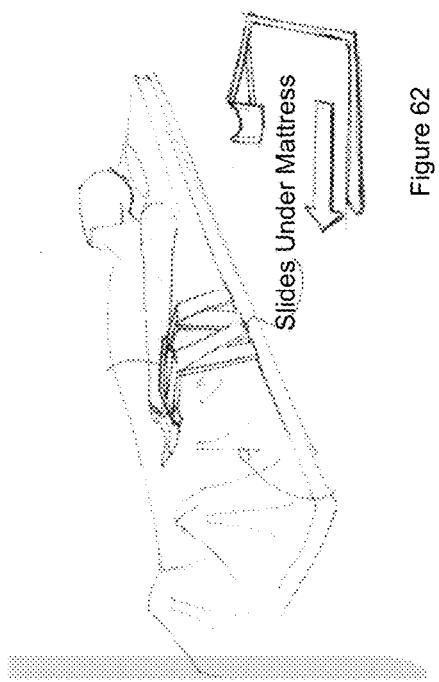
Figure 68:
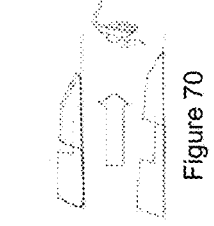
FIGS. 64-71 show various embodiments for making an arm support adjustable in length.
Figure 69:
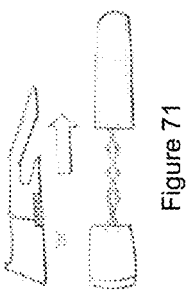
Figure 66:
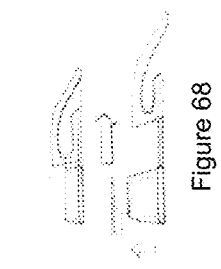
Figure 67:
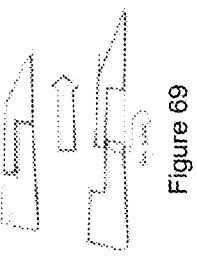
Figure 70:
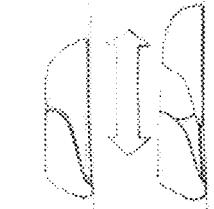
Figure 71:
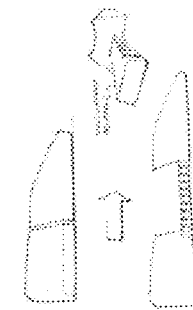
Figure 64:
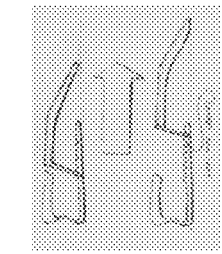
Figure 65:
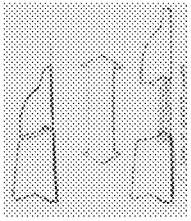

As shown in FIGS. 34-57, additional variations may be used. For example, the wrist flexing section may be cantilevered from the arm support section, FIG. 25, or the arm support section may be cantilevered from the wrist flexing section, FIG. 38. The arm support may also be designed to mate with the post-op wrist support, FIGS. 54-57.

Referring to FIGS. 58-63, the arm support may also be designed as a one-piece table and arm support. For example, as shown in FIGS. 45-50, a bottom portion of the arm support slides under a mattress to position a top portion of the arm support in position to support an arm for catheterization.

Lastly, as shown in FIGS. 64-71, there are varying ways to make the arm support adjustable along its length.

The foregoing has described an apparatus for supporting an arm during medical procedures such as radial catheterization and carpal tunnel procedures. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

I claim:

1. An apparatus configured to support an arm during a medical procedure, comprising:
    (a) an arm support section configured to support an arm of a patient;
    (b) an intermediary valley section connected to a second end of the arm support section;
    (c) a wrist flexing section connected to a second end of the intermediary valley section and configured to promote a downward flexing of the wrist, the wrist flexing section including a raised middle section and a downwardly extending portion, the raised middle section lies in substantially the same plane as the arm support section and allows the wrist of a patient to flex downwardly such that a back of the patient's hand lies adjacent to the downwardly extending portion; and
    (d) a hand-hold section connected to the wrist flexing section and configured to hold the wrist in the downward flexing position.

2. The apparatus according to claim 1, wherein the arm support section includes a downwardly extending tang extending from a first end of the arm support section, the downwardly extending tang configured to elevate and stabilize the arm support section.

3. The apparatus according to claim 1, wherein the arm support section includes a valley extending between a first end of the arm support section and the second end of the arm support section, the valley being configured to accommodate the patient's elbow in a substantially contact free position to alleviate pressure on the elbow.

4. The apparatus according to claim 1, wherein the intermediary valley section extends between the arm support section and the wrist flexing section and creates a space between the apparatus and a forearm of the patient to permit a radial compressive device to placed around the patient's arm.

5. The apparatus according to claim 1, wherein the hand-hold section includes a handle connected to first and second sides of the wrist flexing section and extending across a downwardly extending portion of the wrist flexing section substantially parallel thereto to permit a patient's fingers to wrap around the handle and hold the patient's hand in position between the handle and the downwardly extending portion.

6. The apparatus according to claim 1, wherein the wrist flexing section is disposed at an angle relative to a center line of the apparatus of about five to about twenty degrees.

7. An apparatus configured to support an arm during a medical procedure, comprising:
    (a) an arm support section configured to support an arm of a patient;
    (b) a wrist flexing section connected to the arm support section by an intermediary valley section, the wrist flexing section including a middle section and a downwardly extending portion; and
    (c) a hand-hold section connected to at least one side of the wrist flexing section and configured to hold the wrist in a downward flexing position, wherein a portion of the arm support section and the middle section are elevated and lie substantially in the same plane to create a space between the intermediary valley section and a forearm of a patient and to allow the patient's wrist to flex downwardly such that a back of the patient's hand lies adjacent to the downwardly extending portion.

8. The apparatus according to claim 7, wherein the wrist flexing section is disposed at an angle relative to a center line of the apparatus of about five to twenty degrees.

9. The apparatus according to claim 7, wherein the hand-hold section includes a handle extending substantially parallel to a downwardly extending portion of the wrist flexing section.

10. A method for securing a patient's arm in position for a medical procedure, comprising the steps of:
    (a) providing an apparatus, having:
        (i) an arm support section; and
        (ii) a wrist flexing section, the wrist flexing section includes a raised middle section and a downwardly extending portion, the raised middle section lies in substantially the same plane as the arm support section and allows the wrist of a patient to flex downwardly such that a back of the patient's hand lies adjacent to the downwardly extending portion;
    (b) placing the patient's arm on the apparatus such that a portion of the patient's arm rests on the arm support section;
    (c) flexing the patient's wrist downwardly and sliding the patient's hand under a hand-hold section extending from at least one side of the wrist flexing section; and
    (d) securing the patient's hand, thereby securing the patient's wrist in a downwardly extending position.

11. The method according to claim 10, further including the step of resting a patient's wrist on the middle section of the wrist flexing section.

12. The method according to claim 10, wherein the step of flexing the patient's wrist further includes sliding the patient's hand between the hand-hold section and the downwardly extending portion of the wrist flexing section.

13. The method according to claim 12, wherein the step of securing the patient's hand includes the step of securing the hand between the downwardly extending portion and the hand-hold section.

* * * * *